United States Patent [19]
Williams et al.

[11] Patent Number: 5,993,814
[45] Date of Patent: Nov. 30, 1999

[54] AGENTS FOR INHIBITION OF CHEMOATTRACTANT

[75] Inventors: Timothy J. Williams; Peter J. Jose; David A. Griffiths-Johnson; John J. Hsuan, all of London, United Kingdom

[73] Assignee: Imperial College of Science, Technology & Medicine, London, United Kingdom

[21] Appl. No.: 08/615,232

[22] PCT Filed: Sep. 14, 1994

[86] PCT No.: PCT/GB94/02006

§ 371 Date: Aug. 13, 1996

§ 102(e) Date: Aug. 13, 1996

[87] PCT Pub. No.: WO95/07985

PCT Pub. Date: Mar. 23, 1995

[30] Foreign Application Priority Data

Sep. 12, 1993 [GB] United Kingdom ............... 9318984
Apr. 29, 1994 [GB] United Kingdom ............... 9408602

[51] Int. Cl.$^6$ ..................... C07K 16/24; A61K 39/395
[52] U.S. Cl. ................... 424/145.1; 530/387.1; 530/387.9; 514/2; 514/8; 514/12; 514/885; 424/139.1
[58] Field of Search ................ 530/350, 387.1, 530/387.9; 514/2, 8, 12, 885; 424/139.1, 145.1

[56] References Cited

U.S. PATENT DOCUMENTS

| | | | |
|---|---|---|---|
| 3,447,978 | 6/1969 | Bluhm | 149/2 |
| 5,079,228 | 1/1992 | Tyler | 514/12 |
| 5,514,555 | 5/1996 | Springer et al. | 435/7.24 |

FOREIGN PATENT DOCUMENTS

| | | |
|---|---|---|
| PCT/CA94/00528 | 3/1992 | WIPO . |
| WO 95/31467 | 11/1995 | WIPO . |

OTHER PUBLICATIONS

Yoshimura et al, FEBS Letters 224 (2) Feb. 1989, 487–493.

The Journal of Experimental Meicine, vol. 179, Mar. 1, 1994, pp. 881–887, P.J. Jose et al., 'Eotaxin: A potent Eosinophil Chemoattractant Cytokine detected in a guinea pig model of allergic airways inflammation'.

Biochemical and Biophysical Research Communications, vol. 197, No. 3, Dec. 30, 1993, Duluth, Minnesota, US, 1167–1172, D.A. Griffiths–Johnson et al 'The Chemokine, Eotaxin, activates guinea–pig eosinophils in vitro and causes their accumulation into the lung in vivo'.

Immunology, vol. 79, No. 2, Jun. 1993, pp. 312–318, P.D. Colins et al. 'Eosinophil accumulation induced by human Interleukin–8 in the guinea pig in vivo'.

Biological Abstracts, vol. 84, No. 9 1987, Philadelphia PA, US; abstract no. 87994, ISODA, MIDORI Eosinophil Chemotactic activity of beta–galactosicase, p. AB–544.

The Journal of experimental medicine, vol. 176, No. 6, Dec. 1, 1992, pp. 1489–1495, A. ROT et ak ; RANTES and macrophage inflammatory protein–lalpha induce the migration and activation of normal human eosinophil granulocytes.

The Journal of Experimental Medicine, vol. 176, No. 2, Aug. 1, 1992, pp. 587–592, Yoshikazu Kameyoshi et al 'Cytokine RANTES release by Thrombin–stimulated platelets is a potent attractant for human eosinophils'.

Chemical Abstracts, vol. 117, No. 11, Sep. 14, 1992, Columbus, Ohio, US;I abstract No. 109899k, Kuna, P. Et al 'RANTES, a monocyte and T lymphocyte chemotactic cytokine releases histamine from human basophils' p. 705; column L.

American Review of Respiratory Disease, vol. 137, No. 4, Apr. 1988, pp. 948–954, A. Lellouch–Tubiana et al 'Eosinophil recrutiment into guinea pig lungs after PAF–acether and Allergen administration'.

Faccioli et al, "The accumulation of $^{111}$In–eosinophils induced by inflammatory mediators, in vivo", Immunology 73:222–227 (1991).

Weg et al, "A Monoclonal Antibody Recognizing Very Late Activation Antigen–4 Inhibits Eosinophil Accumulation In Vivo", J. Exp. Med. 177:561–566 (1993).

Dahinden et al, "Monocyte Chemotactic Protein 3 Is a Most Effective Basophil– and Eosinophil activating Chemokine", J. Exp. Med. 179:751–756 (1994).

Van Damme et al, "Structural and Functional Identification of Two Human, Tumor–derived Monocyte Chemotactic Proteins (MCP–2 and MCP–3) Belonging to the Chemokine Family", J. Exp. Med. 176:59–65 (1992).

Opdenakker et al, "Human Monocyte chemotactic protein–3 (MCP–3): molecular cloning of the cDNA and comparison with other chemokines", Biochemical and Biophysical Research Communications 191(2):535–542 (1993).

Cunningham et al.(1989) Science, vol. 244, pp. 1081–1085.

George et al. (1988) Macromolecular Sequencing & Systems ch. 12, pp. 127–149., Alan r. Liss, Inc.

Reeck et al.(1987) Cell vol. 50, p. 667.

Bourie et al. (1990) Science. vol. 247 pp. 1306–1310.

Ponath et al. (1996) J. Clin. Invest. vol. 97, No. 3, pp. 604–612.

Jore et al. (1994) Biochem. Biophys. Res. Comm. vol. 205, No. 1, pp. 788–794.

*Primary Examiner*—Prema Mertz
*Attorney, Agent, or Firm*—Nixon & Vanderhye, P.C.

[57] ABSTRACT

A chemoattractant protein called "eotaxin" is capable of attracting eosinophils and of inducing eosinophil accumulation and/or activation in vitro and in vivo. Various types of agents that inhibit or otherwise hinder the production, release or activity of eotaxin may be used therapeutically in the treatment of asthma and other inflammatory diseases.

2 Claims, 8 Drawing Sheets

```
         10        20        30        40        50        60        70
HPGIPSACCFRVTNKKISFQRLKSYKIITSSKCPQTAIVFEIKPDKMICADPKXXWVQDAKKYLDQISQXTKP
```
N-TERMINL ANALYSES                                    T4      T5      T6

T1            T2            T2                                T7

```
         10        20        30        40        50        60        70
HPGIPSACCFRVTNKKISFQRLKSYKIITSSKCPQTAIVFEIKPDKMICADPKKKWVQDAKKYLDQISQTTKP
```

```
HPGIPSACCFRVTNMKISFQRLKSYKIITSSKCPQTAIVFEIKPDKNICADPKxxWVQDAKKYLDQISQxTKP

QPDAINAPVTCCYNFTNRKISVQRLASYRRITSSKCPKEAVIFKTIVAKEICADPKQKWQDSMDHLDKQTQTPKT
DSVSIPITCCFNVINRKIPIQRLESYTRITNIQCPKEAVIFKTKRGKEVCADPKERWVRDSMKHLDQIFQNLKP
       KSTTCCYRFINRKIPKQRLESYRRTTSSHCPREAVIF  K DKEICADPTQKWVQDFMKNLDKKTQTPKL

GVNTP  TCCYTF   NKQIPLKRVKGYERITSSRCPQEAVIFRTLKNKEVCADPTQKWVQDYIAKEDQRTQQKQN

SLAADTPTACCFSYTSRQIPQNFIADY  FETSSQCSKPGVIFLTKRSRQVCADPSEEWVQKYVSDLELSA
PMGSDPPTACCFSYTARKLPRNFVVDY  YETSSLCSQPAVFQTKRSKQVCADPSESWVQEYVYDLELN
SPYSSDTTPCCEAYIARPLPRAHIKEY  FYTSGKCSNPAVVFVTRKNRQVCANPEKKWVREYINSLEMS
```

FIG. 9

AGENTS FOR INHIBITION OF CHEMOATTRACTANT

CROSS REFERENCE TO RELATED APPLICATION

This is a 371 of WO 95/07985.

The present invention relates to a chemotactic cytokine. The accumulation of eosinophil leukocytes is a characteristic feature of IgE-mediated allergic reactions such as allergic asthma, rhinitis and eczema. Eosinophil accumulation also occurs in non-allergic asthma. The immediate bronchoconstriction in response to a provoking stimulus in the asthmatic involves mast cell activation and the release of constrictor mediators. This is followed after several hours in some individuals by a late bronchoconstrictor response associated with a massive influx of eosinophils (1). Repeated provocation results in chronic inflammation in the airways and a marked hyper-responsiveness to constrictor mediators. The magnitude of both the late response and the chronic hyper-responsiveness correlates with the numbers of eosinophils present in the lung (2,3).

The present invention provides a chemoattractant protein capable of attracting eosinophils and of inducing eosinophil accumulation and/or activation in vitro and in vivo. The chemoattractant protein of the present invention is designated "eotaxin".

Eotaxins are proteins of the C—C branch of the platelet factor 4 superfamily of chemotactic cytokines. Within the C—C branch of the platelet factor 4 superfamily of chemotactic cytokines, or chemokines, certain members have the property of attracting eosinophils in vitro and some may induce eosinophil accumulation in vivo. For example, the chemokines RANTES and MIP-1α attract eosinophils in vitro while MCP-1 and MIP-1β do not. ("RANTES" denotes Regulated upon Activation in Normal T cells Expressed and Secreted, "MIP" denotes Macrophage Inflammatory Protein, and "MCP" denotes Monocyte Chemo-attractant Protein.)

Naturally-occurring cytokines within the platelet factor 4 superfamily of chemotactic cytokines may have marked inter—the amino acid sequence of the protein, and in the carbohydrate modifications of the protein, while retaining the same characteristic functional properties. Similar variations in structure may occur in cytokines obtained from different individuals within the same species. Many chemokines within the C—C branch of the platelet factor 4 superfamily show promiscuity of receptor binding, and the ability of different chemokines to bind to the same receptor is not necessarily dependent on a high degree of homology at the amino acid level. Accordingly, both interspecies and intraspecies variations in protein length, amino acid sequence and carbohydrate modifications are generally to be expected for eotaxins.

The ability to attract eosinophils and to induce eosinophil accumulation and/or activation in vitro and in vivo is a characteristic property of eotaxins. Furthermore, eotaxins generally show substantially no attractive effect for neutrophils in vivo. The eosinophil chemoattractant effect may be an inter-species effect, for example, guinea-pig eotaxin appears to be potent in inducing chemotaxis of human eosinophils in vitro.

An eotaxin may be obtained from an appropriate body fluid, for example, from bronchoalveolar lavage fluid obtained from a human or non-human subject, particularly an allergic subject after an allergen challenge, either experimentally induced or naturally incurred. Other sources of eotaxins are, for example, inflammatory exudate fluids and in vitro cultures of macrophages, lymphocytes, neutrophils, mast cells, airway epithelial cells, connective tissue cells, vascular endothelial cells and eosinophils themselves.

For example, an eotaxin may be obtained from a sensitised guinea-pig after allergen challenge. Guinea-pig models are useful as they share many common features with the asthmatic response in man. Eotaxin obtainable from bronchoalveolar lavage fluid of a sensitised guinea-pig by sequential HPLC purification generally has a molecular weight in the range of from 6–16 kDa. (As indicated above, intraspecies molecular weight variations of this order of magnitude are observed in members of the platelet factor 4 superfamily.)

The amino acid sequence of a guinea-pig eotaxin is set out in SEQ.ID. NO. 1, SEQ.ID. NO. 2 and in FIGS. 7 and 8 of the accompanying drawings. Other guinea-pig eotaxins will generally have at least 50% overall homology with the sequence shown in SEQ.ID. NO. 1 (FIG. 7) at the amino acid level. The homology may be at least 60%, for example at least 70%, for example at least 80% with the sequence set out in SEQ.ID. NO. 1 and in FIG. 7.

Percentage homology in the present case is calculated on the basis of amino acids that are identical in corresponding positions in the two sequences under investigation. Conservative substitutions are not taken into account. In the calculation of percentage homology of a putative eotaxin molecule under investigation with the sequence shown in SEQ.ID. NO. 1 (FIG. 7) or with SEQ.ID. NO. 2 (FIG. 8) if the molecule under investigation has a different length from the eotaxin set out in SEQ.ID. NO. 1 or SEQ.ID. NO. 2 (FIG. 7 or FIG. 8), then the calculation is based on the amino acids in the portion of the molecule under investigation that overlaps with the sequence shown in SEQ.ID. NO. 1 (FIG. 7) or SEQ.ID. NO. 2 (FIG. 8). Software packages for the alignment of amino acid sequences and the calculation of homology are available commercially, for example, the "Bestfit" program available from Genetics Computer Group Sequence Analysis Software, Madison, Wis., U.S.A.

Unless specified otherwise, the specific values of percentage homology between eotaxin and other chemotactic cytokines given in the present specification have been calculated on the basis of the eotaxin set out in SEQ.ID. NO. 1 (FIG. 7).

As indicated above, eotaxins obtainable from species other than guinea-pigs, for example humans, will exhibit inter-species differences of the type demonstrated by other members of the C—C branch of the platelet factor 4 superfamily of chemokines, for example, differences in protein length, amino acid sequence and carbohydrate modifications. There may, for example, be variations in the C- and/or N-terminal residues.

For example, it is expected that the molecular weight of an eotaxin from a species other than guinea-pig will generally fall within the range of from 6 kDa to 16 kDa, but in some cases an eotaxin may have a molecular weight less than 6 kDa or more than 16 kDa.

Similarly, it is expected that in general an eotaxin from a species other than guinea-pig will have at least 40% overall homology with the sequence set out in SEQ.ID. NO. 1 and in FIG. 7. The homology may be at least 50%, for example at least 60%, for example at least 70%, for example at least 80% with the sequence set out in SEQ.ID. NO. 1 and in FIG. 7. There may, however, be eotaxins from species other than guinea-pigs that have less than 40% homology with SEQ.ID. NO. 1 (FIG. 7).

Eotaxins may be identified by any one or more of the characteristics set out above, in particular by their ability to attract and/or active eosinophils in vitro and cause their accumulation and/or activation in vivo. A characteristic that assists the identification of a molecule as an eotaxin is the lack of attractive effect on neutrophils.

The present invention provides a method of determining the ability of a substance to induce eosinophil accumulation and/or activation in vivo, that is to say, a method for testing putative eotaxins, which comprises administering the substance, generally intradermally, to a test animal previously treated with labelled, for example $^{111}$In-labelled, eosinophils and subsequently determining the number of labelled eosinophils at a skin site.

One in vitro method that may be used to test a putative eotaxin for the ability to attract and/or activate eosinophils in vitro is the ability of the substance to increase eosinophil intracellular calcium levels. Other general methods for determining chemotactic activity in vitro may be used to test putative eotaxins in vitro.

Confirmation that an eosinophil attractant is an eotaxin may also be made by consideration of sequence homology of that protein with the sequence set out in SEQ.ID. NO. 1 (FIG. 7) and/or with the sequence set in SEQ.ID. NO. 2 (FIG. 8) and/or by consideration of the structural relationship between the protein and the guinea-pig eotaxin.

As mentioned above, RANTES and MIP-1α are both eosinophil activators. Eotaxin has functional similarities but low structural homology with RANTES and MIP-1α (31% homology with MIP-1α at the amino acid level calculated on the basis of SEQ.ID. No. 1 (FIG. 7); 32% homology when calculated on the basis of the overlapping sequences and 26% homology with RANTES at the amino acid level calculated on the basis of SEQ.ID. No. 1 (FIG. 7); 27% homology when calculated on the basis of the overlapping sequences). An eotaxin can be distinguished from RANTES and MIP-1α not only by the degree of homology but also by the overall differences in sequence and structure.

In addition to full-length eotaxin molecules, the present invention also provides molecules that comprise less than a full length eotaxin sequence. Such molecules (called "fragments" herein) may be polypeptides or peptides. For use as an eotaxin substitute, a fragment should retain one or more of the biological activities of the parent molecule.

Eosinophils contain an armoury of chemicals necessary for killing parasites. These chemicals have been implicated in the damage to airway epithelium that occurs in asthma and may relate to the observed changes in airway function (26,27). From our studies we suggest that eotaxins should be considered as important mediators of eosinophil accumulation in vivo. Macrophages, lymphocytes, neutrophils, mast cells, airway epithelial cells, connective tissue cells, vascular endothelial cells and eosinophils themselves are likely candidates as the source of the eosinophil chemoattractant activity generated in the lung. Platelets may also have a role as it has been shown that they can release C—C chemokines (22). Further, an early platelet deposition may be involved in the subsequent eosinophil accumulation in vivo (28,29) and there is evidence that platelet-activating factor induces the synthesis of an unidentified eosinophil chemoattractant in vivo (30). In this respect, it is of interest that platelet-derived growth factor can induce gene expression of C—C chemokines in fibroblasts (31). Furthermore, the C—C chemokines have been implicated in wound healing (18). This may be important in the sub-epithelial basement membrane fibrosis that is a prominent feature of the asthmatic lung. Thus, eotaxins may be involved in both eosinophil accumulation and in chronic structural changes in the lung.

Eotaxins may have an important role in asthma and in other diseases having an inflammatory component where eosinophil accumulation and/or activation is a prominent feature, for example, rhinitis and eczema, especially allergic eczema. Accordingly, agents that inhibit or otherwise hinder the production, release or action of eotaxins have potential as selective therapeutic agents. Such agents and their therapeutic use are part of the present invention.

Such agents include inhibitors that affect the interaction of an eotaxin with eotaxin receptors, for example, by binding to an eotaxin or to an eotaxin receptor. An example of such an inhibitor is receptors themselves which, on administration, can bind an eotaxin and prevent its interaction with naturally-occurring receptors. Such inhibitory receptors may be soluble or insoluble. Receptors which are not involved in cell activation may be bound to, or induced on, cells. Such receptors may also be used to remove endogenous eotaxin.

Further examples of agents that affect the interaction of eotaxins with eotaxin receptors are receptor antagonists, and antibodies, both antibodies directed against (capable of binding with) an eotaxin and antibodies directed against an eotaxin receptor, especially monoclonal antibodies. Any other agent that inhibits or otherwise hinders the binding of an eotaxin to an eotaxin receptor also has therapeutic potential, for example, any other agent that binds to an eotaxin or to an eotaxin receptor. Further agents that have therapeutic potential are those that prevent or reduce activation of eotaxin receptors.

Further agents that inhibit or otherwise hinder the action of eotaxins are those that change the structure of an eotaxin such that it is no longer able to bind to an eotaxin receptor, for example, an enzyme or other agent that degrades eotaxin specifically.

Receptor promiscuity is common among chemokines, so although it is essential that a receptor is capable of binding an eotaxin, the receptor need not necessarily be eotaxin-specific. For example, a receptor may bind MIP-1α, RANTES and/or other eosinophil attractant chemokines as well as an eotaxin.

As indicated above, possibilities for therapeutic intervention include the use of a receptor to which an eotaxin binds, especially a soluble receptor. It may be advantageous to use an eotaxin-specific receptor. Further possibilities for therapeutic intervention include receptor antagonists, for example, based on 3-dimensional structures or the amino acid sequences of eotaxins and/or of eotaxin receptors, and agents found to inhibit eotaxin or other agonists binding to or activating eotaxin receptors. For example, a receptor antagonist or an agonist inhibitor may be a polypeptide in which the sequence of a full-length naturally-occurring eotaxin has been modified, for example, by amino acid substitution, or may be a fragment of an eotaxin (that is to say, a polypeptide or small peptide comprising part of the amino acid sequence of a naturally-occurring eotaxin), or a modified fragment of an eotaxin, for example, modified by amino acid substitution.

Furthermore, knowledge of the sequence and/or structure of eotaxins either alone or in combination with knowledge of the sequence and/or structure of other chemokines that bind to the same receptor(s) as eotaxins, provides useful information for the design of therapeutic agents.

Agents that prevent or inhibit eotaxin synthesis or release may also be used therapeutically. Such agents and their use are also part of the present invention.

All inhibitors of eotaxin activity, synthesis and release, including soluble receptors, antibodies, antagonists and inhibitors of agonist binding, and their use are part of the present invention.

The present invention accordingly provides an agent that inhibits or otherwise hinders the production, release or action of an eotaxin, especially an agent as described above, for use as a medicament. The invention also provides the use of an agent that inhibits or otherwise hinders the production, release or action of an eotaxin, especially an agent as described above, in the manufacture of a medicament for the treatment of asthma or another disease having an inflammatory component, particularly with accumulation of eosinophils, for example, rhinitis or eczema, especially allergic eczema.

The use of the structural and sequence information relating to eotaxins in the design of therapeutically and diagnostically useful agents, for example, in computer-aided design based on the three dimensional structure of eotaxins is part of the present invention.

Putative inhibitors of eotaxin activity may be screened using in vivo and in vitro assays based on inhibition of chemoattraction and/or accumulation and/or activation of eosinophils by eotaxins. Some general methods for testing the activity of a compound for an inhibitory effect on the activity of a chemoattractant cytokine in vitro are known. Such assays may be used to determine the inhibitory action of a putative inhibitor on in vitro effects induced in eosinophils by eotaxins.

Assays that are suitable for screening putative eotaxin inhibitors include, for example, inhibition in vitro of elevation of intracellular calcium levels induced in cells by eotaxin. The method of the present invention for determining the ability of a substance to induce eosinophil accumulation and/or activation in vivo, that is to say, a method for testing putative eotaxins, may also be used to determine the ability of a substance to inhibit eosinophil accumulation and/or activation induced in vivo by an eotaxin: an animal is pretreated with labelled eosinophils, an eotaxin and a putative inhibitor are administered, and the number of labelled eosinophils at a skin site are determined subsequently. The eotaxin is generally administered intradermally, and the putative inhibitor may be administered by the same route or by a different route, for example systemically.

Examples of in vitro and in vivo assays both for the determination of eotaxin activity and for the determination of eotaxin inhibitory activity are described herein. For example, Example 1 gives a detailed protocol for the in vivo assay of the present invention, and Example 4 gives detailed protocols of various assays. The assays described herein may be used as such, or may be modified as required. Assays may be used alone or in combination to establish eotaxin and eotaxin-inhibitory activity. A putative inhibitors may be any of the types of molecules described above, including receptors, for example, soluble receptors, antibodies, and antagonists and inhibitors of agonist binding. Methods for testing putative inhibitors of eotaxins are also part of the present invention.

A further aspect of the present invention is a pharmaceutical preparation comprising, as active ingredient, an agent that inhibits or otherwise hinders the production, release or action of an eotaxin, in admixture or in conjunction with a pharmaceutically suitable carrier. Such agents are described above and include, for example, an inhibitor of eotaxin synthesis or release, a soluble eotaxin receptor, an eotaxin receptor antagonist or an inhibitor of an eotaxin receptor agonist, an antibody against eotaxin or an antibody against an eotaxin receptor.

The invention further provides a method of treating asthma and other inflammatory diseases, comprising the administration of an effective amount of an agent that inhibits or otherwise hinders the production, release or action of an eotaxin. The agent may be as described above, for example, an inhibitor of eotaxin synthesis or release, a soluble eotaxin receptor, an eotaxin receptor antagonist or an inhibitor of an eotaxin receptor agonist, or an antibody against eotaxin or against an eotaxin receptor.

The present invention also provides assays for eotaxins and for anti-eotaxin antibodies, especially immunoassays and in particular ELISAs (enzyme-linked immunosorbent assays). The invention provides, for example, an immunoassay for an antigen, characterised in that the antigen is an eotaxin, and also provides an immunoassay for an antibody, characterised in that the antibody is an anti-eotaxin antibody. The invention also provides assays for eotaxins that are analogous to immunoassays for eotaxins but that use a specific-binding partner other than an antibody. In such specific-binding partner assays an eotaxin receptor may be used instead of an anti-eotaxin antibody.

In an immunoassay, an anti-eotaxin antibody may, for example, be coated on a solid surface to enable capture and hence detection of eotaxin. An anti-eotaxin antibody may be used in an assay for the detection of antibodies to eotaxin, for example, in a competitive antibody assay. A labelled eotaxin or a derivative thereof, for example, a recombinant eotaxin or a synthetic peptide comprising part of the amino acid sequence of an eotaxin may be used in a competitive antigen assay for eotaxin or may be used to coat a solid surface in a capture assay for antibodies to eotaxin. The many different types of assay format are well described in the literature of the art, see for example "ELISA and Other Solid Phase Immunoassays, Theoretical and Practical Aspects" Eds. Kemeny D. M. & Challacombe S. J., John Wiley, 1988. (36). Assays using an eotaxin receptor instead of an anti-eotaxin antibody may be carried out analogously.

The present invention provides a process for the production of an eotaxin, which comprises obtaining bronchoalveolar lavage fluid obtained from a human or non-human animal challenged with a provoking stimulus, for example, from a human suffering from allergic or non-allergic asthma, or other lung disease, or a guinea-pig sensitised with a foreign protein, and isolating a fraction showing eosinophil chemoattractant activity. One method of isolating an eotaxin-containing fraction of bronchoalveolar lavage fluid is sequential cation exchange, size exclusion and reversed phase HPLC systems. The desired fraction generally contains a polypeptide having a molecular weight in the range from 6–6 kDa. Purity may be verified by SDS-PAGE. If desired, the authenticity of the substance obtained may be determined by comparison of the amino acid sequence thereof with the amino acid sequence set out in SEQ.ID. NO. 1 or SEQ.ID. NO. 2 (FIG. 7 or FIG. 8).

Eotaxins may be obtained according to the above procedure from other sources, for example, from inflammatory exudate fluids, or from in vitro cultures of macrophages, lymphocytes, neutrophils, mast cells, airway epithelial cells, connective tissue cells, vascular endothelial cells and eosinophils themselves.

Alternatively, a full-length eotaxin, or a part (fragment) of an eotaxin, for example, a polypeptide or peptide fragment, may be produced by chemical synthesis, for example, according to the Merryfield technique. A further method for producing a full-length eotaxin or a part thereof is by recombinant DNA technology. All methods of producing eotaxin are part of the present invention.

To produce a full-length eotaxin polypeptide or a polypeptide (or peptide) fragment by recombinant DNA technology, a nucleic acid sequence encoding the polypeptide is inserted into an expression vector under the control of appropriate control sequences. A recombinant polypeptide may then be expressed using a prokaryotic expression system, for example, in *E. coli*, or using a eukaryotic cell system, in which case the resulting polypeptide may be glycosylated. Such techniques are standard see, for example Sambrook, J., Fritisch, E. F. and Maniatis T., Molecular Cloning A Laboratory Manual, Cold Spring Harbor Laboratory Press, 1989 (37).

A nucleic acid encoding all or part of an eotaxin polypeptide may be obtained by screening a library prepared from suitable cells, for example, cells from allergen-challenged guinea-pig or human lung. Screening may be carried out using a probe comprising sequences characteristic of an eotaxin, in particular, sequences that distinguish the eotaxin from other related cytokines, for example, RANTES and MIP-1α. It may be preferable to use a long probe, for example, a probe comprising a nucleic acid sequence encoding a full-length eotaxin polypeptide.

Alternatively, the polypeptide sequence of an eotaxin may be used to design oligonucleotide primers, for example, degenerate primers. Primers may, for example, comprise bases less specific in their interaction than the naturally-occurring bases, for example, inosine may be used. Examples of primers are the sense sequence

5' TGC TGT TTC CGI GTI ACI AAC AAA (SEQ.ID.NO. 3)

based on the amino acid sequence CCFRVTNK, and the anti-sense sequence

5' CAT CTT GTC IGG CTT IAT TTC (SEQ.ID. NO. 4)

based on the amino acid sequence EIKPDKM. Such primers may be used for amplification of reverse transcribed mRNA by the polymerase chain reaction. This provides cDNA probes for screening libraries, for example, as described above, to isolate full length eotaxin clones. Primers may include codons chosen on the basis of known species preference.

As indicated above, derivatives of naturally occurring eotaxins are also part of the present invention. Such derivatives include polypeptides that have one or more of the following modifications relative to a naturally-occurring eotaxin:

(i) elongation or shortening at the C-terminus;
(ii) elongation or shortening at the N-terminus;
(iii) deletion and/or insertion of internal sequences;
(iv) amino acid substitutions, for example at the C- and/or N-terminus; and
(v) a different pattern of glycosylation. (There is, for example, a potential O-glycosylation site at residue 70.)

Such derivatives may function as agonists for structure/activity relationship studies or as receptor antagonists.

Anti-eotaxin antibodies and anti-eotaxin receptor-antibodies, both polyclonal and monoclonal, may be produced according to standard techniques, for example, Kohler & Milstein (38). A full-length eotaxin may be used as antigen, or it may be preferred to use a fragment of an eotaxin in order to produce an antibody to a specific antigenic determinant. A naturally occurring eotaxin may used as antigen. Alternatively, a recombinant or synthetic eotaxin or eotaxin polypeptide or peptide may be used.

BRIEF DESCRIPTION OF THE DRAWINGS

FIGS. 1 to 18 of the accompanying drawings illustrate the present invention. The following is a brief description of the Figures. A more detailed description of the Figures is given below and in the Examples section of this specification.

FIG. 1: Protocol for the generation and assay of eosinophil chemoattractant activity in vivo.

FIG. 2: Time course of generation of eosinophil chemoattractant activity in lungs of sensitized guinea-pigs after antigen challenge.

FIGS. 3, 4 and 5 all relate to the purification of eotaxin from bronchoalveolar lavage (BAL) fluids:

FIG. 3: Final reversed phase HPLC profile showing absorbance at 214 nm and the acetonitrile gradient.

FIG. 4: Measurement of $^{111}$In-eosinophil chemoattractant activity of the fractions obtained on HPLC chromatography.

FIG. 5: Measurement of $^{111}$In-neutrophil chemoattractant activity; lack of significant activity observed.

FIG. 6: SDS-PAGE analysis of C18 reversed phase HPLC fractions 50–56.

FIGS. 7 and 8: Amino acid sequences of an isolated guinea-pig eotaxin.

FIG. 9: Comparison of the eotaxin sequence of FIG. 7 with human MCP-1(SEQ ID NO:5), MCP-2(SEQ ID NO:6), MCP-3 (21) (SEQ ID NO:7), guinea-pig MCP-1 (24) (SEQ ID NO:8), human MIP-1α (SEQ ID NO:9), MIP-1β (SEQ ID NO:10) and RANTES (SEQ ID NO:11) (18) showing conserved residues (shaded).

FIG. 10: Comparison of $^{111}$In-eosinophil accumulation in vivo using guinea-pig eotaxin and the recombinant human proteins RANTES, MIP-1α and MCP-1.

FIG. 11 (Inset): Inhibition of the binding of $^{125}$I-RANTES to guinea-pig eosinophils in vitro induced by eotaxin and RANTES but not by a member of the C-X-C branch of chemokines, IL-8.

FIGS. 12, 13 and 14 illustrate the potential of blocking the response to guinea-pig eotaxin. This makes use of the fact that human RANTES, whilst competing with eotaxin for binding sites, does not activate guinea-pig eosinophils.

FIG. 12: Elevation of intracellular calcium levels in human eosinophils in vitro induced by eotaxin, RANTES and, at high concentration only, MCP-1.

FIG. 13: Elevation of intracellular calcium levels in guinea-pig eosinophils in vitro induced by eotaxin, but not human RANTES and MCP-1.

FIG. 14: Representative traces showing inhibition of guinea-pig eotaxin-induced elevation of intracellular calcium levels in guinea-pig eosinophils in vitro by the previous exposure of the same cells to human RANTES. Inset:

FIG. 15: Values (mean±SEM) for four separate eosinophil preparations.

FIG. 16: Dose response curve showing inhibition of guinea-pig eotaxin-induced elevation of intracellular calcium levels in guinea-pig eosinophils in vitro by the previous exposure of the same cells to human RANTES.

FIG. 17: Histogram showing comparison of in viva response of guinea-pig eosinophils to eotaxin, RANTES and RANTES plus eotaxin co-injected intradermally.

FIG. 18: Histogram showing number of eosinophils and neutrophils in bronchoalveolar lavage fluid (BAL) after administration of guinea-pig eotaxin as an aerosol to guinea-pig airways.

As in allergic asthmatic patients, exposure of sensitised guinea-pigs to aerosolised antigen results in an immediate phase of bronchoconstriction with associated mast cell degranulation followed, in some individuals, by a late phase of bronchoconstriction and airway hyper-responsiveness (4–7). Although clearly no one model mimics all the features of the human disease, the guinea-pig model shares common features with the asthmatic response in man and has been extensively used to investigate possible mechanisms (7). In particular, in both guinea-pig and man, the immediate response to allergen triggers the subsequent accumulation in the lung of high numbers of eosinophils. Experiments were designed to detect the appearance in the lung of chemoattractants that may be responsible for the accumulation of eosinophils. A strategy was employed that has previously been applied to the identification of neutrophil chemoattractants in inflammatory exudates (8–10).

Figure 1:
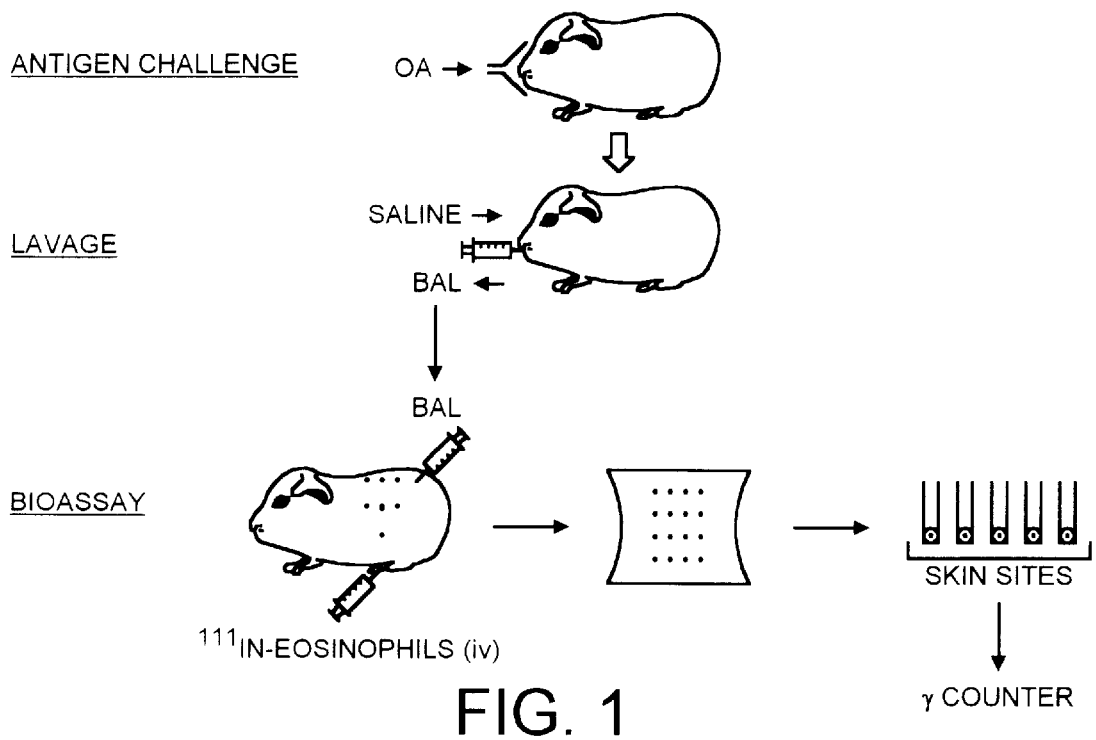

Guinea-pigs were sensitised with intraperitoneal ovalbumin on day 1 followed by a short exposure of their lungs to aerosolised ovalbumin at day 8. On day 15–21 animals were challenged with aerosolised ovalbumin and killed at different intervals using a barbiturate overdose. Immediately after death the airways were lavaged with saline. The bronchoalveolar lavage (BAL) fluid was centrifuged to remove cells, and supernatants were either stored at −20° C. for assay or subjected to purification. Eosinophil chemoattractant activity in BAL fluid samples or HPLC fractions was tested by injecting them intradermally into assay guinea-pigs previously given intravenous injections of $^{111}$In-eosinophils (11, 12). After a 2 or 4 h interval, assay animals were killed and the punched out skin sites were counted in a gamma-counter (FIG. 1).

Figure 2:
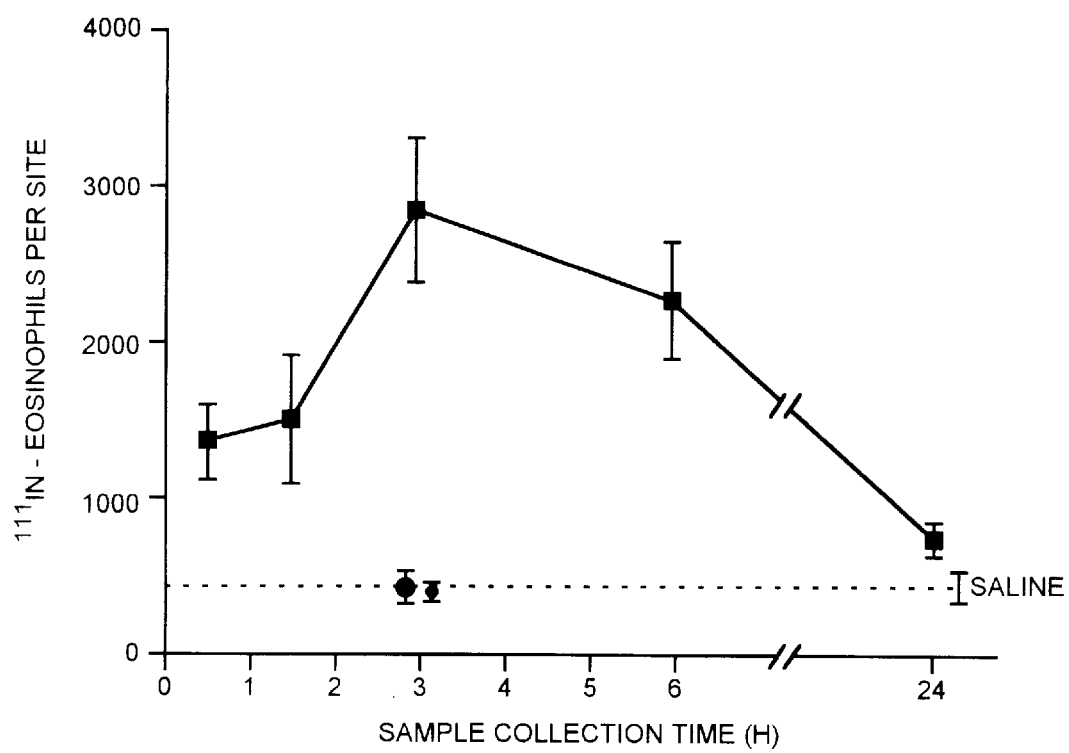

FIG. 2 shows the time-course of appearance of eosinophil chemoattractant activity in BAL fluid. Significant activity was observed 30 min after antigen challenge. Activity increased up to 3 h, remained high at 6 h, but was not significant in 24 h samples. Control samples (BAL fluid from sham-sensitised/challenged or sensitised/sham-challenged guinea-pigs) taken at 3 h had no significant activity.

Figure 3:
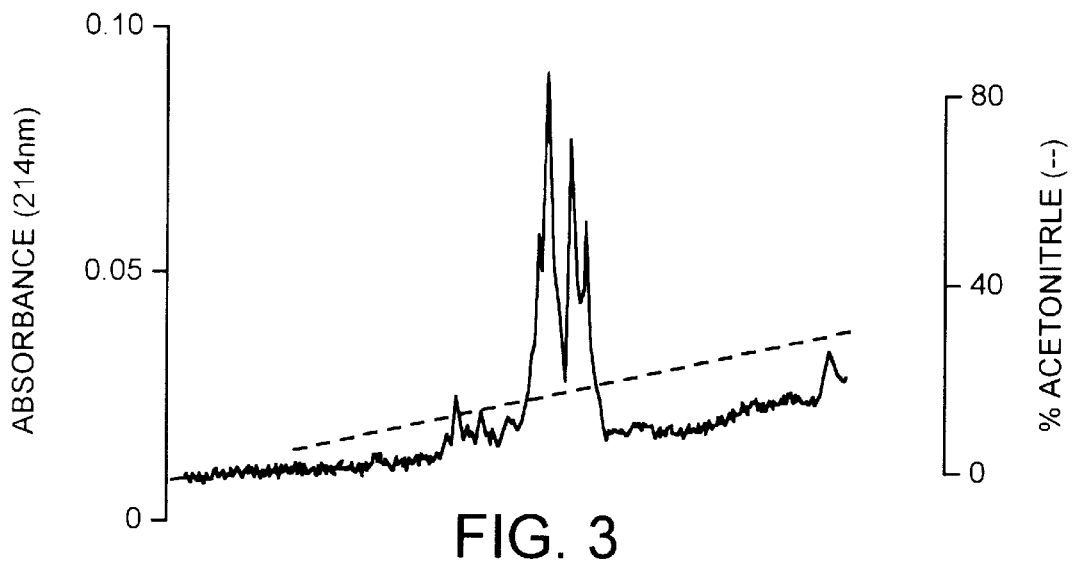
Figure 4:
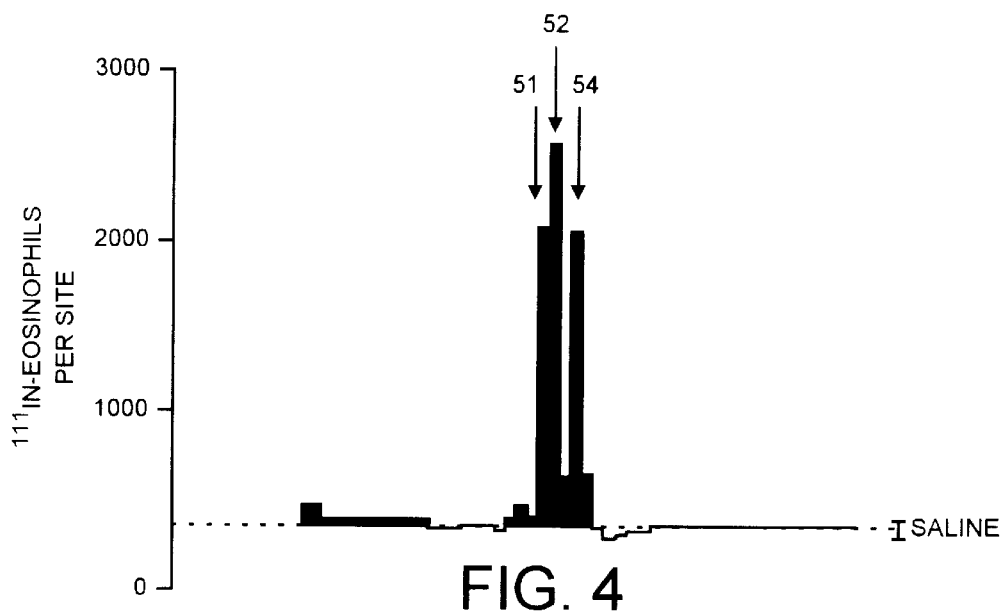
Figure 5:
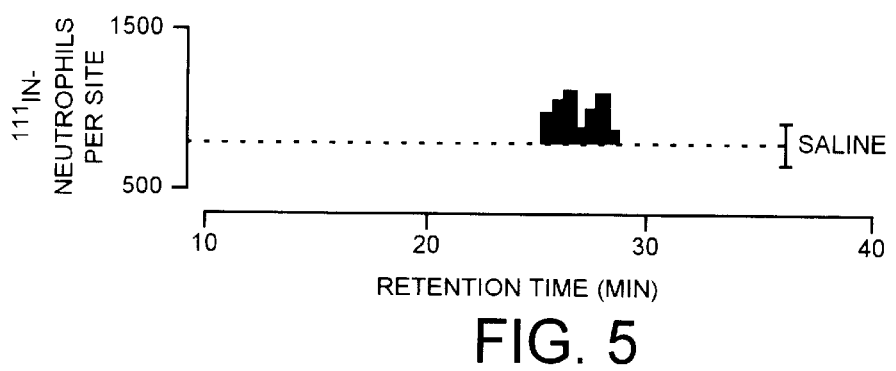

Eosinophil chemoattractant activity, which we termed eotaxin, was purified from 3 h BAL fluid by sequential cation exchange, size exclusion and reversed phase HPLC using the in vivo $^{111}$In-eosinophil accumulation assay to measure the activity of fractions throughout. Eotaxin eluted as a single discreet peak of bioactivity from both the cation exchange and the size exclusion steps, indicating a strongly cationic protein of 7–14kDa. Reversed phase chromatography separated eosinophil chemoattractant activity into two peaks (fractions 51+52 and fraction 54), which were associated with discreet peaks of protein absorbance (FIGS. 3 and 4). Selectivity for eosinophils was shown by the lack of significant neutrophil chemoattractant activity in these fractions as measured by the accumulation of $^{111}$In-neutrophils in the skin assay (FIG. 5). Histological examination of skin injected with eotaxin (2 pmol) demonstrated eosinophil accumulation at 4 and 24 h, particularly around small blood vessels (haematoxylin and eosin stains).

Figures 6, 7, 8:
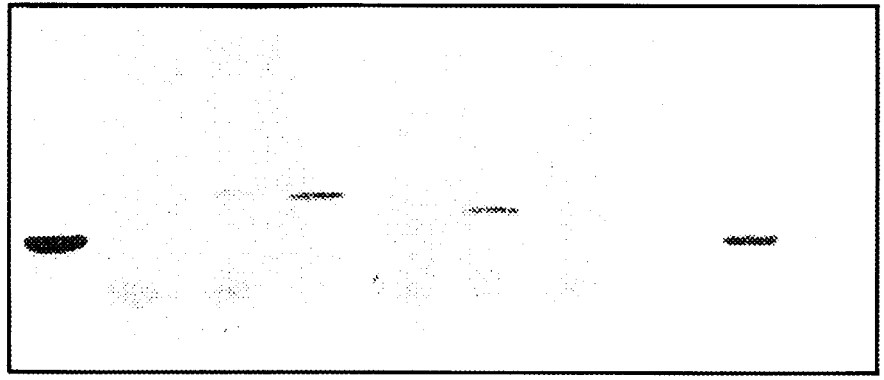

SDS-PAGE analysis revealed a single protein band in each of fractions 51, 52 and 54 (FIG. 6). The protein in fractions 51 and 52 was slightly larger than that in fraction 54. This was confirmed by mass analysis in which the major signals were at approximately 8.81 and 8.38 kDa respectively (see Example 3). N-terminal sequencing of fractions 51, 52 and 54 revealed identical amino acid sequences (see FIG. 7). The N-terminal 37 residue sequence of eotaxin as set out in SEQ.ID. NO. 1 and FIG. 7 shows 57% homology with human monocyte chemotactic protein (MCP-1 (13), otherwise known as MCAF (14) and JE (15)). Tryptic peptides of fraction 54 were also sequenced and readily aligned by comparison with human MCP-1 to give the virtually complete sequence of eotaxin with an overall homology of 53%, see FIG. 7. It is likely that the variations in molecular mass reflect differential glycosylation as the four mass signals obtained (two major and two minor, see Example 3) are all different from each other by multiples of approximately 220 mass units. The sequence contains no N-glycosylation sites, but a potential O-glycosylation site at position 70 has been identified (see Example 3). Human MCP-1 also exhibits heterogeneity on SDS-PAGE due to differences in the O-linked carbohydrate modification (16).

The platelet factor 4 superfamily of chemotactic cytokines, or chemokines, is characterised by four conserved cysteines. The relative position of the two N-terminal cysteines allows the subdivision of this superfamily into the C-X-C chemokines (eg. IL-8 (17)) which are predominantly neutrophil chemoattractants and the C—C chemokines (eg. MCP-1, RANTES, MIP-1α and MIP-1β (18)) which are chemotactic for leukocytes other than neutrophils. Eotaxin is a member of the C—C branch of chemokines. The greatest homology (53%) is with human MCP-1 which, in the limited in vitro studies to date, has been reported to be inactive on human eosinophils (19,20) and with the recently described human MCP-2 (54%) and MCP-3 (51% homology calculated on the basis of SEQ.ID. No. 1 (FIG. 7); 54% homology when calculated on the basis of the overlapping sequences) (21). Homology with other human C—C chemokines (FIG. 9) is: MIP-1β (37% calculated on the basis of SEQ.ID. No. 1 (FIG. 7); 39% when calculated on the basis of the overlapping sequences), MIP-1α (31% calculated on the basis of SEQ.ID. No. 1 (FIG. 7); 32% when calculated on the basis of the over-lapping sequences) and RANTES (26% calculated on the basis of SEQ.ID. No. 1 (FIG. 7); 27% when calculated on the basis of the overlapping sequences). The latter two proteins have recently been shown to be potent eosinophil activators in vitro (20,22) whereas MIP-1β activates lymphocytes in vitro (23) but apparently not eosinophils (20). Eotaxin shows the greatest structural homology with human MCP-1, MCP-2 and MCP-3. Eotaxin has functional similarities, but relatively low homology, when compared with RANTES and MIP-1α. Eotaxin is clearly a distinct molecule from guinea-pig MCP-1; the latter has recently been cloned (24) and it has only a 43% homology with the eotaxin sequence, see FIG. 9. Guinea-pig MCP-1 was shown to be chemotactic for monocytes but was not tested on eosinophils (24). Interestingly, eotaxin has a 41% homology with a C—C protein whose gene is expressed in mouse mast cells and upregulated 2 h after the interaction between IgE and antigen (25). No functional activity has been reported for this protein but it is distinct (51% homology) from mouse MCP-1/JE (25).

Figure 10:
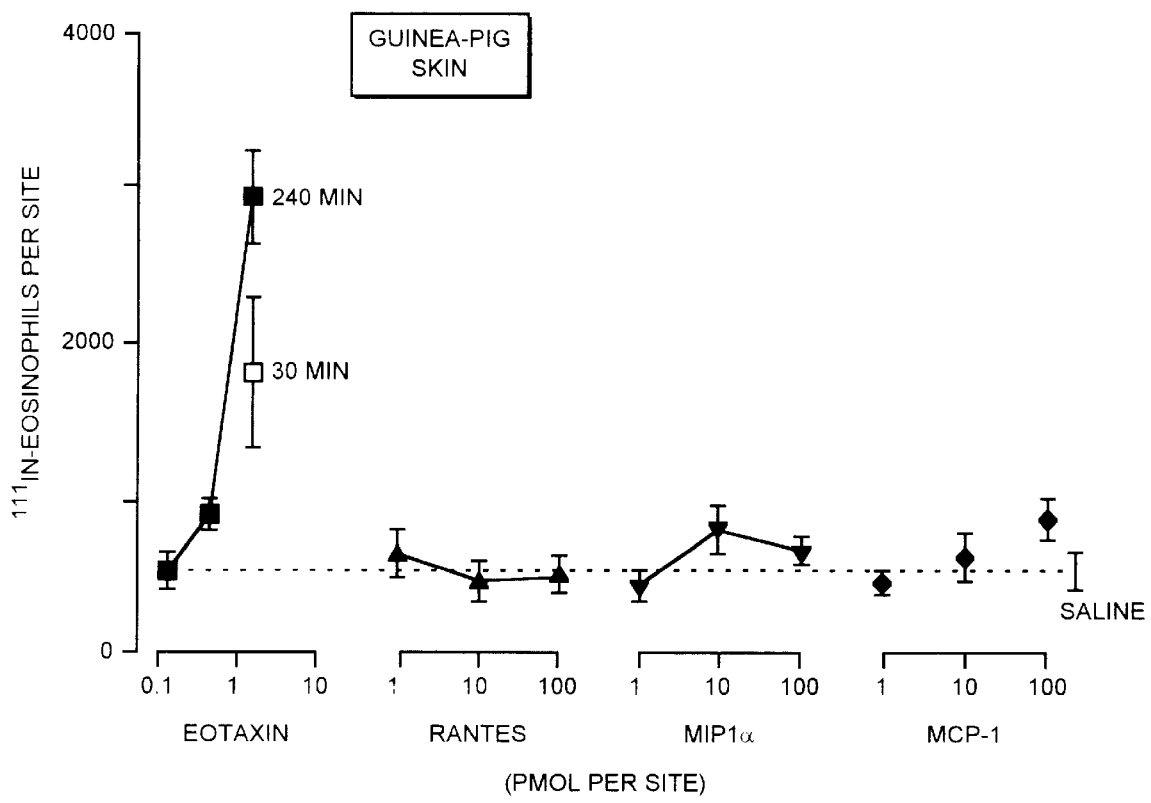
Figure 11:
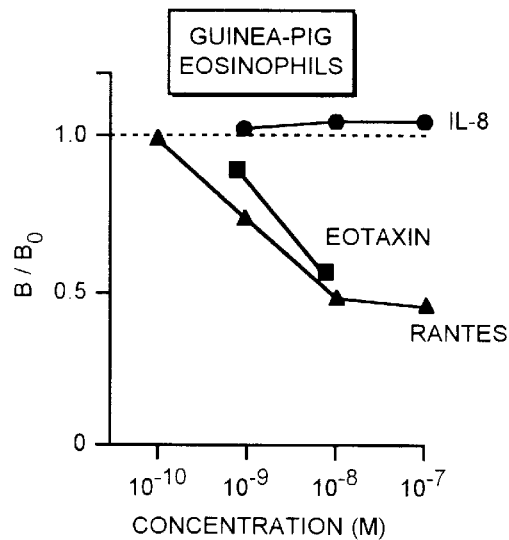
Figure 12:
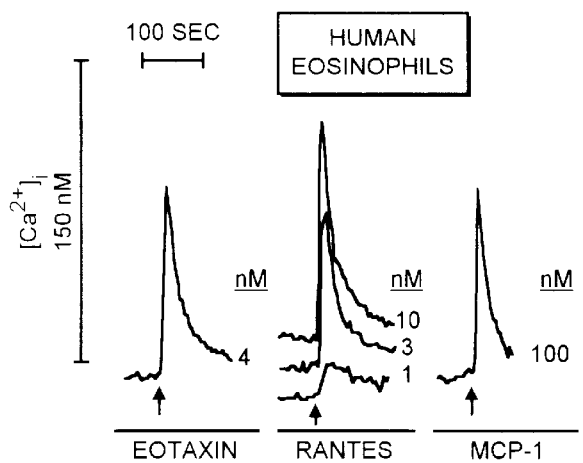
Figure 13:
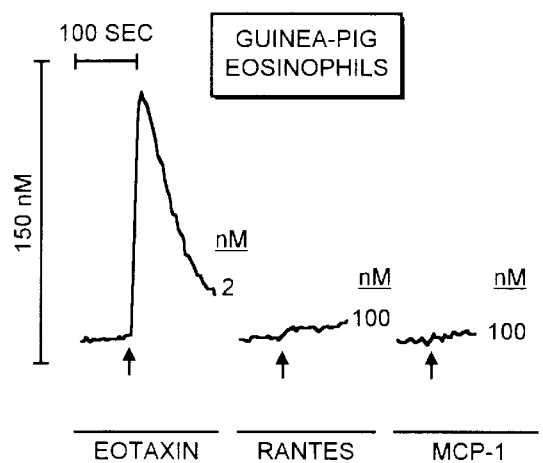

Guinea-pig eotaxin was very potent in inducing eosinophil accumulation in vivo: 1–2 pmol/skin site giving a 730±140% response (mean±s.e.m., n=18 animals) compared with saline-injected sites. Further, marked eosinophil accumulation was seen within 30 minutes of intradermal injection (FIG. 10). This is supported by experiments in vitro. The effect of eotaxin on eosinophils in vitro was shown by (i) inhibition of binding of $^{125}$I-RANTES to guinea-pig cells (FIG. 11), (ii) elevation of cytoplasmic calcium in human and guinea-pig cells (FIGS. 12 and 13) and (iii) chemotaxis of human eosinophils in a Boyden chamber system: the chemotactic responses to eotaxin and RANTES were of similar magnitude over the range 0.1–3.0 nM. In contrast to eotaxin, human recombinant MCP-1 and RANTES did not induce guinea-pig eosinophil responses in vivo or in vitro (FIGS. 10 and 13). This may reflect a species difference although RANTES did bind to guinea-pig eosinophils without inducing activation (FIG. 11, inset in FIG. 10). Eotaxin has a similar potency to RANTES on human eosinophils whereas MCP-1 is either inactive (20) or active only at high doses (FIG. 12). Thus, eotaxin has a potent direct effect on both human and guinea-pig eosinophils.

Figure 14:
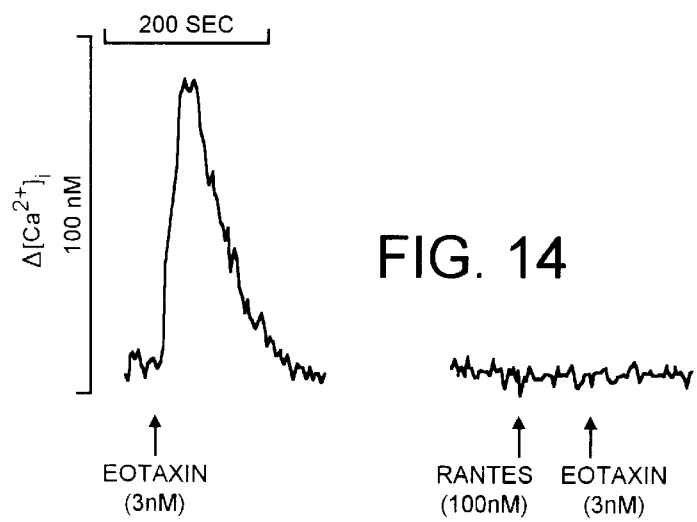
Figure 15:
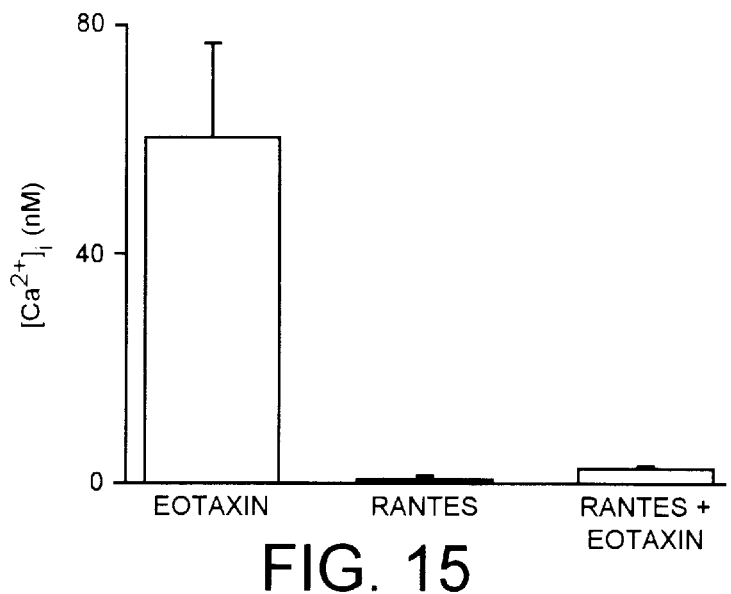
Figure 16:
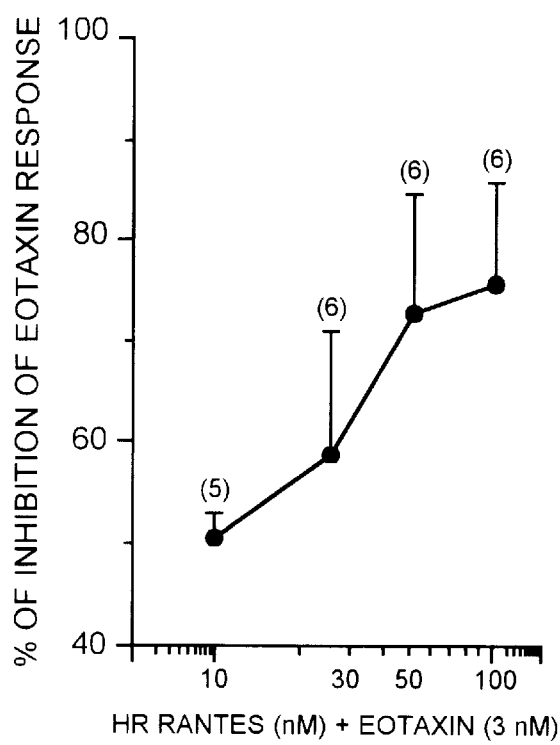
Figure 17:
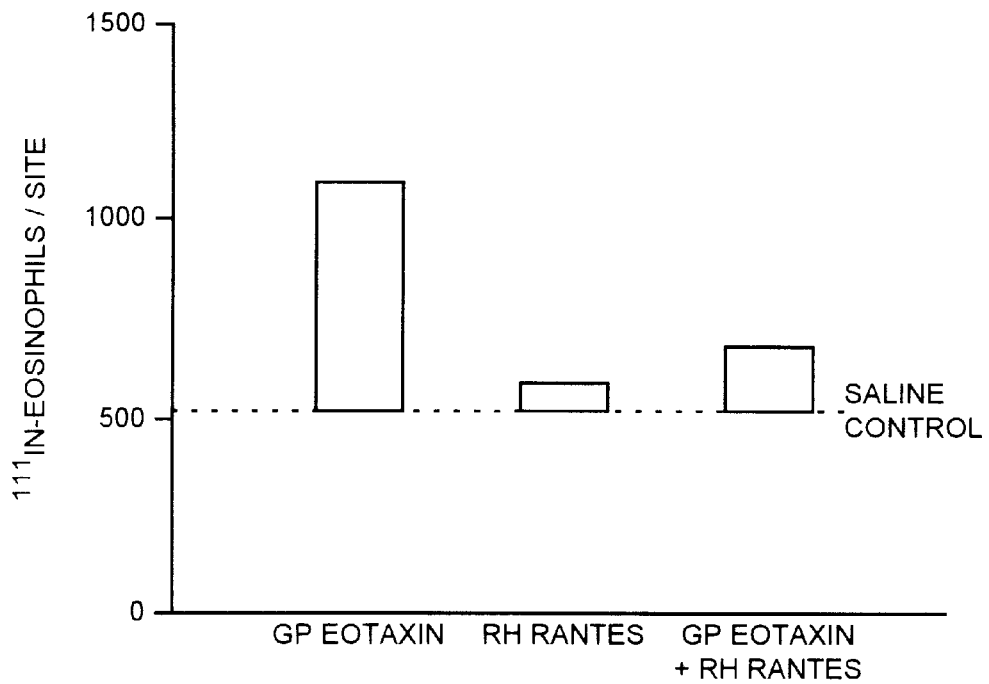

Responses of guinea-pig eosinophils to guinea-pig eotaxin in vitro and in vivo can be inhibited by human RANTES. FIGS. 14, 15 and 16 show the response of FURA-2-loaded guinea-pig eosinophils to guinea-pig eotaxin before and after the addition of human RANTES. The eotaxin-induced increase in intracellular calcium concentration is reduced to a substantial degree when the cells are first exposed to human RANTES, which itself fails to induce a response. FIG. 17 shows that human RANTES, when coinjected with the eotaxin, reduces the accumulation of guinea-pig eosinophils induced by eotaxin in guinea-pig skin in vivo. The results support our observations that eotaxin exhibits competitive binding with radiolabelled human RANTES on guinea-pig eosinophils and that eotaxin is a potent functional stimulant whereas RANTES is not. Accordingly, RANTES appears to act as a receptor antagonist for eotaxin on guinea-pig eosinophils.

Figure 18:
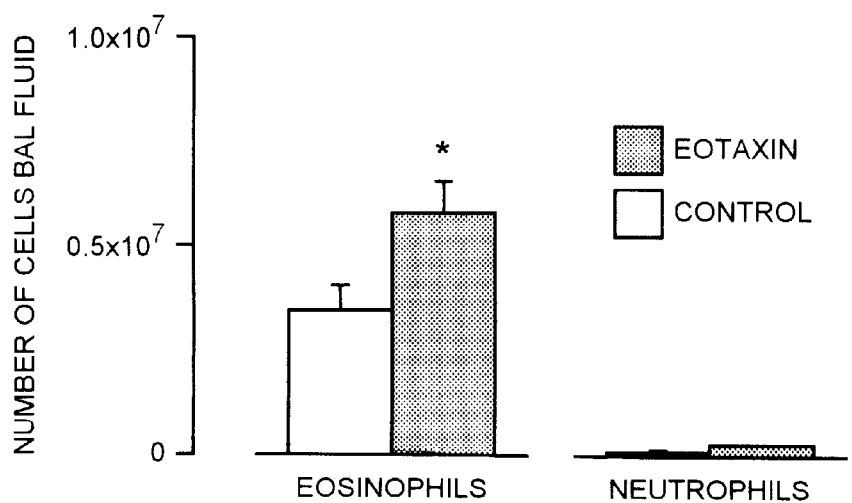

FIG. 18 shows that eosinophils accumulate in guinea-pig airways in vivo within 24 hours of the administration of aerosolized guinea-pig eotaxin, whereas substantially no accumulation of neutrophils is observed.

The following Examples illustrate the present invention.

EXAMPLE 1
Production and Testing of Bronchoalveolar Lavage Fluid

METHODS: Male Dunkin Hartley guinea-pigs (300–400 g) were sensitised with intraperitoneal ovalbumin (OA, 1 mg) on day 1 followed by exposure to aerosolised antigen (2% OA for 5 min using an ultrasonic nebuliser) on day 8 (6). On day 15–21, animals were pretreated with an antihistamine to prevent acute fatality (pyrilamine, 10 mg kg$^{-1}$, i.p.) and challenged by exposure to aerosolised antigen (1% OA for 20 min). At different times after antigen challenge animals were treated with atropine (0.06 mg kg$^{-1}$, i.p.) to prevent broncho-constriction and killed with a barbiturate overdose. Broncho-alveolar lavage was performed with 4 ml saline. Samples were centrifuged to remove cells and the supernatant stored at $-20°$ C. prior to assay. BAL samples were assayed by intradermal injection (0.1 ml) into guinea-pigs previously given intravenous injections of 5×10$^6$ $^{111}$In-eosinophils (elicited in donor animals by repeated intraperitoneal injections of horse serum and purified on discontinuous Percoll gradients, >94% purity) (11,12). After 4 hours, assay animals were killed and the skin sites punched out for gamma-counting. Data are presented as the mean±s.e.m. and were tested by one way analysis of variance. A p value of <0.05 was considered statistically significant.

RESULTS: FIG. 1 shows, schematically, procedures for the generation and measurement of eosinophil chemoattractant activity in vivo. FIG. 2 illustrates the time course of generation of eosinophil chemoattractant activity in lungs of sensitised guinea-pigs after antigen challenge (filled squares, n=4–10). Activity was measured in an in vivo skin assay of $^{111}$In-eosinophil accumulation in unsensitised guinea-pigs (3 test animals per BAL sample). Significant activity was seen in bronchoalveolar lavage samples taken 0.5, 1.5, 3 and 6 h after antigen challenge (compared to responses to intradermal saline, shown as the dotted line). No significant activity was observed in 24 h samples. No activity was seen in lavage samples obtained 3 h after sham (saline) challenge of sensitised animals (filled circles, n=5) or antigen challenge of sham (saline) sensitised animals (filled diamonds, n=5).

EXAMPLE 2
Purification of Eotaxin from Bronchoalveolar Lavage Fluids

METHODS: Bronchoalveolar lavage (BAL) fluid collected from 25 sensitised guinea-pigs (each lavaged with 4 ml, followed by 2×10 ml, saline) 3 h after antigen challenge (1% OA, 5 min exposure) was applied to a cation exchange HPLC column (Ultropac TSK535CM, 7.5×150 mm). Activity was eluted at approx 1.4M ammonium acetate, pH5.5, and lyophilised for size exclusion HPLC (Ultropac TSK columns SWP, 7.5×75 mm, G4000SW, 7.5×600 mm, and G2000SW, 7.5×600 mm, in series, equilibrated in 0.08% TFA). Activity eluted at approx 7–14 kDa. This was applied to a wide pore (300A) Vydac C18 reversed phase HPLC column (4×250 mm) in 0.08% TFA, eluted with a linear gradient of acetonitrile (0–80% ACN in 0.08% TFA, over 80 mins, at 1 ml min$^{-1}$) and 0.5 min fractions were collected. Aliquots (4%) of each fraction were lyophilised in the presence of carrier protein (BSA, <0.1 ng endotoxin mg$^{-1}$) and redissolved in 0.8 ml saline for testing in the skin bioassays of $^{111}$In-eosinophil and $^{111}$In-neutrophil accumulation over 2 hours (n=4). Eosinophils (99%, 0.5% neutrophils) were elicited with repeated intra-peritoneal injections of horse serum (11,12) and neutrophils (99.4%, 0.6% eosinophils) were elicited with a single intraperitoneal injection of casein (5% w/v, 15 ml) 17 h prior to purification on discontinuous Percoll gradients and labelling with $^{111}$In.

RESULTS: The results are presented in FIGS. 3, 4 and 5. FIG. 3 shows the final reversed phase HPLC profile showing absorbance at 214 nm and the acetonitrile gradient. FIG. 4 shows that eosinophil chemoattractant activity was seen in 2 peaks, corresponding to fractions 51+52 and fraction 54, which corresponded to discreet peaks of absorbance. FIG. 5 shows that no significant neutrophil chemoattractant activity was detected in these fractions. In contrast, guinea-pig C5a des Arg (30% zymosan-activated plasma (11), approx 10 pmol/site) induced the accumulation of both $^{111}$In-eosinophils (5211±893) and $^{111}$In-neutrophils (9872±473). Fractions 50, 53, 55 and 56 consistently gave little or no activity in the guinea-pig skin bioassays of leukocyte accumulation. No significant protein absorbance was detected in the remainder of the gradient (up to 80% acetonitrile).

EXAMPLE 3
Purity, Mass Analysis and Protein Sequence of Eotaxin

METHODS: 2% aliquots of each fraction were lyophilised, redissolved in 10 μl SDS buffer, heated (95° C., 5 min) and 0.3 μl run on 8–25% gradient gels in a Pharmacia Phast System. Gels were visualised with silver staining. Mass analysis was performed on fractions 51, 52 and 54 using a Finnigan MAT Lasermat with α-cyano-4-hydroxycynnamic acid and sinapinic acid matrices. Mass measurements were calibrated internally using protein standards. 5% aliquots of each bioactive fraction (51, 52 and 54) were applied directly to automated N-terminal sequence analysis using fast cycles on an Applied Biosystems 477A containing a microcartridge essentially as described (32). The amino-terminal 37, 35 and 29 residues were obtained for fractions 51, 52 and 54 respectively. No differences between corresponding positions were found. The apparent initial yields of these three analyses were all approximately 7–8 pmol. Thus fractions 51, 52 and 54 contained approx 200 pmol each, assuming 70–80% sequencing yields. Gaps were found at positions 8,9 and 33, consistent with the presence of cysteine residues at these positions. Approximately 30 pmol of fraction 54 was reduced and alkylated by sequential treatment with 1 mM dithiothreitol for 5 min at 50° C. and then 20 mm acrylamide for 30 min at 37° C. before digestion with alkylated trypsin (Promega) in 20 mM Tris/HCl, pH8.8, containing 0.5% Thesit. Peptides were separated using a Reliasil C18 (300 Å, 5 μm) column (1×150 mm) developed with a linear acetonitrile concentration gradient in 0.08% tri-fluoroacetic acid at 50 μl/min on a Microm HPLC system. Purified peptides were subjected to N-terminal sequence analysis as above, but all four cysteine residues were positively identified as the PTH-cys-S-β-propionamide derivative (33). Position 70 gave no PTH derivative in peptides T6 and T7 and is a probable position of O-glyco-sylation.

RESULTS: The results are presented in FIGS. 6, 7, 8 and 9. FIG. 6 is a photograph of the SDS-PAGE gel. For reference, human IL-8 (72 amino acids, approx 8 kDa) was run in lanes A, B and C (12, 2.4 and 0.5 ng/0.3 μl/lane respectively). Laser desorption time of flight mass analysis gave signals at 8.81 kDa (major) and 9.03 kDa (minor) for each of fractions 51 and 52. Fraction 54 gave signals at 8.38 kDa (major) and 8.15 kDa (minor).

FIG. 7 and SEQ.ID. NO. 1 show the amino acid sequence of eotaxin, which was determined by sequencing the intact molecule as well as peptides derived from digestion with trypsin (T). N-terminal analyses showed the highest homology with human MCP-1 (57%) and the tryptic peptides were readily aligned by comparison with the human MCP-1 sequence. FIG. 8 shows the amino acids sequence as confirmed by nucleic acid sequencing. FIG. 9 is a comparison of the eotaxin sequence with human MCP-1, MCP-2, MCP-3 (21), guinea-pig MCP-1 (24), human MIP-1α, MIP-2 and RANTES (18) showing conserved residues (shaded).

EXAMPLE 4
In vitro and in vivo Testing of Eotaxin
METHODS:
(i) Eotaxin was a pool of both peaks of bioactivity (fractions 51+52 and fraction 54) from the final reversed phase HPLC separation described in Example 2 (see FIGS. 3, 4 and 5). $^{111}$In-eosinophil accumulation in guinea-pig skin was measured over 4 h as described in Example 1 (see FIGS. 1 and 2). In the same animals (n=4) additional sites were injected with eotaxin 30 minutes before killing.
(ii) For the binding studies, 4×10$^5$ eosinophils were incubated with 0.1 nM $^{125}$I-RANTES and various concentrations of cold ligand (50 μl at 0° C. for 2 h). The Hank's buffered salt solution contained 30 mM HEPES, 10 mM EDTA, 0.1% sodium azide and 1% BSA at pH7.5. Results are the mean of two assays each done in triplicate.
(iii) For measurement of intracellular calcium levels human and guinea-pig eosinophils (10$^7$cells/ml in Ca$^{2+}$/Mg$^{2+}$-free PBS+0.1% BSA) were loaded with fura-2-acetoxymethyl ester (2.5 μM, 30min at 37° C.). After two washes cells were resuspended at 10$^6$cells/ml in Ca$^{2+}$/Mg$^{2+}$-free PBS containing 10 mM HEPES, 0.25% BSA and 10 mM glucose (pH 7.4). Aliquots were dispensed into quartz cuvettes and the external [Ca$^{2+}$] adjusted to 1 mM with CaCl$_2$. Changes in fluorescence were monitored at 37° C. using a Perkin Elmer LS50 spectrophotometer at excitation wavelengths 340nm and 380nm and emission wavelength 510nm. [Ca$^{2+}$]$_i$ levels were calculated as described previously (34) using the ratio of the two fluorescence readings and a Kd for Ca$^{2+}$ binding at 37° C. of 224nM. Peripheral human eosinophils were prepared as described previously (35) by density centrifugation on Percoll followed by immunomagnetic removal of CD16$^+$ neutrophils using the MACS system. Guinea-pig eosinophils were prepared as described in Example 1 (11,12).
(iv) To test for suppression of eposinophil accumulation in vivo using human RANTES, accumulation of $^{111}$-labelled guinea-pig eosinophils in skin sites was measured as described above. Guinea-pigs were injected with 1.8 pmol eotaxin (n=2), 100 pmol RANTES (n=1) or both 1.8 pmol eotaxin and 100 pmol RANTES (n=2). Intradermal saline was used as control.
(v) For testing of receptor antagonist activity, the fura-2-acetoxymethyl ester-loaded guinea-pig eosinophils were stimulated with 3 nM eotaxin with or without pretreatment with human RANTES.
(vi) To investigate the effect of aerosol exposure of guinea-pigs to eotaxin, naive guinea-pigs were exposed to an aerosol of either eotaxin or a control medium (n=8 per group). Exposure was performed by placing two animals in a single chamber and nebulising 24 pmol of eotaxin dissolved in 10 ml PBS containing BSA carrier protein at 80 μg/ml over a period of 35–40 minutes. Control animals received aerosolised PBS/BSA in the same manner. The animals were killed 20 hours after exposure to eotaxin or control medium. BAL fluid (5×10 ml HBSS, 10 mM EDTA, pH 7.35) was recovered and centrifuged (300 g, 20 min, 4° C.). Total BAL cell count was determined by haemocytometer and differential cell counts performed on stained (DiffQuick) cytospin preparations (3 per animal, 400 cell counts per slide).

RESULTS: The results are presented in FIGS. 10, 11, 12, 13, 14, 15, 16, 17 and 18.

FIG. 10 shows that guinea-pig eotaxin (1.6 pmol) induces significant $^{111}$In-eosinophil accumulation in vivo 30 min (open squares, p<0.01) and 4 h (filled squares, p<0.01) after intradermal injection. In contrast, the recombinant human proteins, RANTES, MIP-1α and MCP-1, at doses up to 100 pmol, were without effect over 4 hours. FIG. 11 inset shows that eotaxin and RANTES, but not the C-X-C chemokine IL-8, inhibit the binding of $^{125}$I-RANTES (B$_0$=14.4%) to guinea-pig eosinophils in vitro. FIG. 17 shows (a) that human RANTES does not induce significant eosinophil accumulation and (b) that human RANTES inhibits to a substantial degree the eosinophil accumulation induced by eotaxin, which suggests that RANTES acts as a receptor antagonist for eotaxin in vivo.

FIG. 12 shows that eotaxin, RANTES and, at high concentration only, MCP-1 induce elevation of intracellular calcium levels in human eosinophils in vitro. Traces are with eosinophils from one donor. In two other donors 2 nM eotaxin gave a mean calcium elevation of 61 nM. In the three donors (97.3±1.2% eosinophils) responses to 10 nM RANTES were 194±74 nM [Ca$^{2+}$]$_i$ and responses to 100 nM MCP-1 were 93±38 nM [Ca$^{2+}$]$_i$. FIG. 13 shows that guinea-pig eotaxin, but not human RANTES or MCP-1, elevates intracellular calcium levels in guinea-pig eosinophils in vitro. Traces are with cells from one donor. In three donors (97.5±0.8% eosinophils) responses were: 2 nM eotaxin, 90±13 nM [Ca$^{2+}$]$_i$; 100 nM RANTES, 2.0±1.7 nM [Ca$^{2+}$]$_i$; 100 nM MCP-1, 3.3±0.7 nM [Ca$^{2+}$]$_i$.

FIG. 14 and the inset FIG. 15 show that prior treatment of guinea-pig eosinophils with RANTES (100 nM) inhibits the increase in intracellular free calcium levels seen when eosinophils are treated with eotaxin (3 nM) alone. RANTES appears to be acting as a receptor antagonist in guinea-pig eosinophils. FIG. 16 is a dose-response curve using 3 nM eotaxin and increasing amounts of RANTES.

FIG. 18 shows that guinea-pig eotaxin, administered as an aerosol, induces eosinophil accumulation in guinea-pig airways in vivo, whereas substantially no accumulation of neutrophils is observed.

REFERENCES 1. de Monchy, J. G. R., Kauffman, H. F., Venge, P., et al. Am. Rev. Respir. Dis. 131, 373–376 (1985).

2. Bousquet, J., Chanez, P., Lacoste, J. Y., et al. N. Engl. J. Med. 323, 1033–1039 (1990).
3. Bradley, B. L., Azzawi, M., Jacobson, M., et al. J. Allergy Clin. Immunol. 88, 661–674 (1991).
4. Dunn, C. J., Elliott, G. A., Oostveen, J. A. & Richards, I. M. Am. Rev. Respir. Dis. 137, 541–547 (1988).
5. Sanjar, S., Aoki, S., Kristersson, A., Smith, D. & Morley, J. Br. J. Pharmacol. 99, 679–686 (1990).
6. Griffiths-Johnson, D. A. & Karol, M. H. Toxicology 65, 283–294 (1991).
7. Campos, H. G. & Church, H. K. Clin. Exp. Allergy 22, 665–666 (1992).
8. Collins, P. D., Jose, P. J. & Williams, T. J. J. Immunol. 146, 677–684 (1991).
9. Beaubien, B. C., Collins, P. D., Jose, P. J., et al. Biochem. J. 271, 797–801 (1990).
10. Jose, P. J., Collins, P. D., Perkins, J. A., et al. Biochem. J. 278, 493–497 (1991).
11. Faccioli, L. H., Nourshargh, S., Moqbel, R., et al. Immunology 73, 222–227 (1991)
12. Weg, V. B., Williams, T. J., Lobb, R. R. & Nourshargh, S. J. Exp. Med. 177, 561–566 (1993).
13. Yoshimura, T., Yuhki, N., Moore, S. K., Appella, E., Lerman, M. I. & Leonard, E. J. FEBS Letts. 244, 487–493 (1989).
14. Furutani, Y., Nomura, H., Notake, M., et al. Biochem. Biophys. Res. Commun. 159, 249–255 (1989).
15. Rollins, B. J., Morrison, E. D. & Stiles, C. D. Proc. Natl. Acad. Sci. USA 85, 3738–3742 (1988).
16. Jiang, Y., Valente, A. J., Williamson, M. J., Zhang, L. & Graves, D. T. J. Biol. Chem. 265, 18318–18321 (1990).
17. Jiang, Y., Valente, A. J., Williamson, M. J., Zhang, L. & Graves, D. T. J. Biol. Chem. 265, 18318–18321 (1990).
18. Schall, T. J. Cytokine 3, 165–183 (1991).
19. Leonard, E. J. & Yoshimura, T. Immunology Today 11, 97–101 (1990).
20. Rot, A., Krieger, M., Brunner, T., Bischoff, S. C., Schall, T. J. & Dahinden, C. A. J. Exp. Med. 176, 1489–1495 (1992).
21. Van Damme, J., Proost, P., Lenaerts, J-P. & Opdenakker, G. J. Exp. Med. 176, 59–65 (1992).
22. Kameyoshi, Y., Dorschner, A., Mallet, A. I., Christophers, E. & Schroder, J-M. J. Exp. Med. 176, 587–592 (1992).
23. Tanaka, Y., Adams, D. H., Hubscher, S., Hirano, H., Siebenlist, U. & Shaw, S. Nature 361, 79–82 (1993).
24. Yoshimura, T. J. Immunol. 150, 5025–5032 (1993).
25. Kulmburg, P. A., Huber, N. E., Scheer, B. J., Wrann, M. & Baumruker, T. J. Exp. Med. 176, 1773–1778 (1992).
26. Frigas, E. & Gleich, G. J. J. Allergy Clin. Immunol. 77, 527–537 (1986).
27. Wegner, C. D., Gundel, R. H., Reilly, P., Haynes, N., Letts, L. G. & Rothlein, R. Science 247, 456–459 (1990).
28. Lellouch-Tubiana, A., Lefort, J., Simon, M-T., Pfister, A. & Vargaftig, B. B. Am. Rev. Respir. Dis. 137, 948–954 (1988).
29. Coyle, A. J., Page, C. P., Atkinson, L., Flanagan, R. & Metzger, W. J. Am. Rev. Respir. Dis. 142, 587–593 (1990).
30. Silva, P. M. R., Martins, M. A., Castro-Faria-Neto, H. C., Cordeiro, R. S. B. & Vargaftig, B. B. J. Pharmacol. Exp. Ther. 257, 1039 (1991).
31. Cochran, B. H., Reffel, A. C. & Stiles, C. D. Cell 33, 939–947 (1983).
32. Totty, N. F., Waterfield, M. D. & Hsuan, J. J. Protein-Science 1, 1215–1224 (1992).
33. Brune, D. C. Anal. Biochem. 207, 285–290 (1992).
34. Grynkiewicz, G., Poenie, M. & Tsien, R. Y. J. Biol. Chem. 260, 3440–3450 (1985).
35. Anwar, A. R. F., Moqbel, R., Walsh, G. M., Kay, A. B. & Wardlaw, A. J. J. Exp. Med. 177, 839–843 (1993).
36. ELISA and Other Solid Phase Immunoassays, Theoretical and Practical Aspects" Eds. Kemeny D. M. & Challacombe S. J., John Wiley, 1988.
37. Sambrook, J., Fritisch, E. F. and Maniatis T., Molecular Cloning A Laboratory Manual, Cold Spring Harbor Laboratory Press, 1989.
38. Kohler & Milstein, Nature 256, 495–497 (1975).

We claim:

1. An agent that inhibits or otherwise hinders the production, release or action of a chemoattractant protein which accomplishes attraction of eosinophils, induction of eosinophil accumulation, and/or activation of eosinophils in vitro and in vivo, said chemoattractant protein consisting of an amino acid sequence as set forth in SEQ ID NO:1 or SEQ ID NO:2, said agent being an antibody which inhibits or otherwise hinders binding of said chemoattractant protein to a receptor.

2. A composition comprising the agent of claim 1 and a pharmaceutically acceptable carrier.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 73 amino acids
      (B) TYPE: amino acid
      (D) TOPOLOGY: linear (ii) MOLECULE TYPE: protein (iii) HYPOTHETICAL: NO (vi) ORIGINAL SOURCE:
      (A) ORGANISM: Cavia porcellus
      (D) DEVELOPMENTAL STAGE: Adult
      (F) TISSUE TYPE: Bronchoalveolar lavage fluid (xi) SEQUENCE DESCRIPTION: SEQ ID NO: 1:

His Pro Gly Ile Pro Ser Ala Cys Cys Phe Arg Val Thr Asn Lys Lys
1           5               10              15

Ile Ser Phe Gln Arg Leu Lys Ser Tyr Lys Ile Ile Thr Ser Ser Lys

```
                20                  25                  30
Cys Pro Gln Thr Ala Ile Val Phe Glu Ile Lys Pro Asp Lys Met Ile
            35                  40                  45

Cys Ala Asp Pro Lys Xaa Xaa Trp Val Gln Asp Ala Lys Lys Tyr Leu
        50                  55                  60

Asp Gln Ile Ser Gln Xaa Thr Lys Pro
65                  70
```

(2) INFORMATION FOR SEQ ID NO: 2:

(i) SEQUENCE CHARACTERISTICS:
        (A) LENGTH: 73 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Cavia cobaya
        (F) TISSUE TYPE: Bronchial lavage fluid (xi) SEQUENCE DESCRIPTION: SEQ ID NO: 2:

```
His Pro Gly Ile Pro Ser Ala Cys Cys Phe Arg Val Thr Asn Lys Lys
1               5                  10                  15

Ile Ser Phe Gln Arg Leu Lys Ser Tyr Lys Ile Ile Thr Ser Ser Lys
            20                  25                  30

Cys Pro Gln Thr Ala Ile Val Phe Glu Ile Lys Pro Asp Lys Met Ile
            35                  40                  45

Cys Ala Asp Pro Lys Lys Lys Trp Val Gln Asp Ala Lys Lys Tyr Leu
        50                  55                  60

Asp Gln Ile Ser Gln Thr Thr Lys Pro
65                  70
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(iii) HYPOTHETICAL: YES (iii) ANTI-SENSE: NO (ix) FEATURE:
        (A) NAME/KEY: modified_base: N is inosine
        (B) LOCATION: 12

(ix) FEATURE:
        (A) NAME/KEY: modified_base: N is inosine
        (B) LOCATION: 15

(ix) FEATURE:
        (A) NAME/KEY: modified_base: N is inosine
        (B) LOCATION: 18

(xi) SEQUENCE DESCRIPTION: SEQ ID NO: 3:

TGCTGTTTCC GNGTNACNAA CAAA                                        24

(2) INFORMATION FOR SEQ ID NO: 4:

(i) SEQUENCE CHARACTERISTICS:
        (A) LENGTH: 21 base pairs

```
            (B) TYPE: nucleic acid
            (C) STRANDEDNESS: single
            (D) TOPOLOGY: linear (ii) MOLECULE TYPE: DNA (primer)

(iii) HYPOTHETICAL: YES (iii) ANTI-SENSE: YES (ix) FEATURE:
            (A) NAME/KEY: modified_base: N is inosine
            (B) LOCATION: 10

(ix) FEATURE:
            (A) NAME/KEY: modified_base: N is inosine
            (B) LOCATION: 16

(xi) SEQUENCE DESCRIPTION: SEQ ID NO: 4:

CATCTTGTCN GGCTTNATTT C                                                       21

(2) INFORMATION FOR SEQ ID NO:5:

(i) SEQUENCE CHARACTERISTICS:
            (A) LENGTH: 76 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Gln Pro Asp Ala Ile Asn Ala Pro Val Thr Cys Cys Tyr Asn Phe Thr
1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

(2) INFORMATION FOR SEQ ID NO:6:

(i) SEQUENCE CHARACTERISTICS:
            (A) LENGTH: 74 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Asp Ser Val Ser Ile Pro Ile Thr Cys Cys Phe Asn Val Ile Asn Arg
1               5                  10                  15

Lys Ile Pro Ile Gln Arg Leu Glu Ser Tyr Thr Arg Ile Thr Asn Ile
            20                  25                  30

Gln Cys Pro Lys Glu Ala Val Ile Phe Lys Thr Lys Arg Gly Lys Glu
        35                  40                  45

Val Cys Ala Asp Pro Lys Glu Arg Trp Val Arg Asp Ser Met Lys His
    50                  55                  60

Leu Asp Gln Ile Phe Gln Asn Leu Lys Pro
65                  70

(2) INFORMATION FOR SEQ ID NO:7:
```

(i) SEQUENCE CHARACTERISTICS:
    (A) LENGTH: 70 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Lys Ser Thr Thr Cys Cys Tyr Arg Phe Ile Asn Lys Ile Pro Lys
1               5                   10                  15

Gln Arg Leu Glu Ser Tyr Arg Arg Thr Thr Ser Ser His Cys Pro Arg
            20                  25                  30

Glu Ala Val Ile Phe Lys Asp Lys Leu Asp Lys Glu Ile Cys Ala Asp
            35                  40                  45

Pro Thr Gln Lys Trp Val Gln Asp Phe Met Lys His Leu Asp Lys Lys
        50                  55                  60

Thr Gln Thr Pro Lys Leu
65                  70

(2) INFORMATION FOR SEQ ID NO:8:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Gly Val Asn Thr Pro Thr Cys Cys Tyr Thr Phe Asn Lys Gln Ile Pro
1               5                   10                  15

Leu Lys Arg Val Lys Gly Tyr Glu Arg Ile Thr Ser Ser Arg Cys Pro
            20                  25                  30

Gln Glu Ala Val Ile Phe Arg Thr Leu Lys Asn Lys Glu Val Cys Ala
            35                  40                  45

Asp Pro Thr Gln Lys Trp Val Gln Asp Tyr Ile Ala Lys Leu Asp Gln
        50                  55                  60

Arg Thr Gln Gln Lys Gln Asn
65                  70

(2) INFORMATION FOR SEQ ID NO:9:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
            35                  40                  45

Val Cys Ala Asp Pro Ser Glu Glu Trp Val Gln Lys Tyr Val Ser Asp
        50                  55                  60

Leu Glu Leu Ser Ala (2) INFORMATION FOR SEQ ID NO:10:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Pro Met Gly Ser Asp Pro Pro Thr Ala Cys Cys Phe Ser Tyr Thr Ala
1               5                   10                  15

Arg Lys Leu Pro Arg Asn Phe Val Val Asp Tyr Tyr Glu Thr Ser Ser
            20                  25                  30

Leu Cys Ser Gln Pro Ala Val Val Phe Gln Thr Lys Arg Ser Lys Gln
            35                  40                  45

Val Cys Ala Asp Pro Ser Glu Ser Trp Val Gln Glu Tyr Val Tyr Asp
            50                  55                  60

Leu Glu Leu Asn
65
```

(2) INFORMATION FOR SEQ ID NO:11:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
            50                  55                  60

Leu Glu Met Ser
65
```